United States Patent [19]

Murao et al.

[11] Patent Number: 4,734,361

[45] Date of Patent: Mar. 29, 1988

[54] LOW TEMPERATURE-SENSITIVE VARIANT OF LACTOBACILLUS BULGARICUS AND A SELECTION METHOD THEREFOR

[75] Inventors: Kanehisa Murao, Higashimurayama; Tsuyoshi Takahashi, Sayama; Tsutomu Kaneko, Higashimurayama, all of Japan

[73] Assignee: Meiji Milk Products Co., Ltd., Tokyo, Japan

[21] Appl. No.: 877,848

[22] Filed: Jun. 24, 1986

[30] Foreign Application Priority Data

Jun. 26, 1985 [JP] Japan .................. 60-137831
Jun. 26, 1985 [JP] Japan .................. 60-137832

[51] Int. Cl.$^4$ .................. C12Q 1/04; C12R 1/225; C12N 1/20; C12N 1/36
[52] U.S. Cl. .................. 435/34; 435/139; 435/245; 435/253; 435/853; 426/43
[58] Field of Search .................. 435/253, 29, 30, 34, 435/139, 259, 260, 800, 853, 245; 426/34, 42, 43, 61

[56] References Cited

U.S. PATENT DOCUMENTS 4,056,637 11/1977 Hagiwara et al. .................. 426/52
4,425,366 1/1984 Sozzi et al. .................. 426/43

Primary Examiner—Elizabeth Weimar

[57] ABSTRACT

The novel variant Lactobacillus bulgaricus sensitive at a lower temperature, that is, showing a weak tendency towards formation of lactic acid in a range of the lower temperature, and the method for the selection of the variant, are disclosed. By employing the variant, it is possible to produce a fermented milk or lactic acid beverage in which the rate of increase in the sour taste after preservation at a lower temperature is significantly lowered.

Cultures of the variant Lactobacillus bulgaricus have been deposited with the Fermentation Research Institute, Agency of Industrial Science and Technology and accorded the number of FERM BP-1041.

3 Claims, 4 Drawing Figures 1) 43° C 2) 25° C

1) ACIDITY OF LACTIC ACID (%)

2) D(−) LACTIC ACID (%)

LOW TEMPERATURE-SENSITIVE VARIANT OF LACTOBACILLUS BULGARICUS AND A SELECTION METHOD THEREFOR

BACKGROUND OF THE INVENTION

1. Field of the Invention

This invention relates to a novel microorganism and a method for the selection thereof. More particularly, it relates to a strain *Lactobacillus bulgaricus* OLL 1074 which is sensitive to a lower temperature in the meaning that it shows a weak tendency towards lactic acid formation at a lower temperature range, and the method for the selection thereof.

The invention also relates to a novel fermented milk or lactic beverage, the method for the preparation thereof and, more particularly, to such beverage obtained by employing the strain *Lactobacillus bulgaricus* OLL 1074 which is sensitive at a lower temperature in the sense that it shows a weak tendency towards lactic acid formation at a lower temperature range, and the method for the preparation thereof.

2. Description of the Prior Art

The yoghurt is a typical fermented milk product known from old and produced by using the strain *Lactobacillus bulgaricus* and the strain *Streptococcus thermophilus* as the main starters. That is, the starting milk material known as yoghurt mix is inoculated with the aforementioned lactic acid bacteria starters and fermented at 40° to 46° C. for several hours. As the fermented product has reached a proper acidity, it is stored in cold state for stopping fermentation and marketed in this state.

Although fermentation of the yoghurt for forming lactic acid is considerably suppressed by such cold preservation, it is not suppressed completely. Even during cold preservation, lactic acid is produced gradually to increase the sour taste so that it is very difficult to maintain the fresh sour taste proper to the newly manufactured yoghurt during the subsequent preservation and distribution periods.

While it is known to sterilize the yoghurt immediately after manufacture thereof to enhance its keeping quality, the yoghurt obtained in this way does not containg live bacteria so that the merit proper to the yoghurt that it contains a live microorganism is lost. As other methods for preventing the increase in the acidity of the yoghurt during preservation thereof, it is also known to heat the yoghurt for a certain period of time and at a temperature higher than the high side growth cessation limit temperature of the lactic acid bacteria and lower than the temperature for complete extinction thereof (Japanese Laying-open Patent Publication No. 6745-1975) or to make use as the starter of a variant M-13 incapable of fermenting lactose for lactic acid formation and artificially transformed from the strain *Lactobacillus jugurti* (Japanese Laying-open Patent Publication No. 38187-1979). However, with the method described in the Laying-open Patent Publication No. 6745-1975, the process is complicated since there is involved a step of preserving a batch of material at a lower temperature, heating and again cooling it, thus entailing a consumption of an excess heat energy, while it is also difficult to control the temperature and the number of live bacteria. With the method described in the Laying-open Patent Publication No. 38187-1979, since the fermentable sugar of the variant *Lactobacillus jugurti* need be added to the culture medium, it is necessary to adjust the suger to a target acidity by a laborious operation. In addition, it is not possible with the method to prepare the plain type yoghurt for which an increasing demand is raised among general consumers.

SUMMARY OF THE INVENTION

It is a primary object of the invention to select and isolate a variant *Lactobacillus bulgaricus* which is subject to only a reduced rate of increase of lactic acid when the biomass is inoculated to the culture medium of the cow's milk, incubated, cooled and preserved at a lower temperature.

It is also an object of the present invention to provide a fermented milk or lactic acid beverage in which, by making use of the low temperature sensitive variant of the *Lactobacillus bulgaricus*, the desirable sour taste proper to the just manufactured yoghurt is prevented from being intensified on preservation at lower temperatures and may be maintained during the preservation and distribution periods.

The present inventors have directed their attention to the mechanism for the increase in lactic acid content during preservation of the yoghurt and succeeded in isolating a variant *Lactobacillus bulgaricus* which is sensitive at a lower temperature in the sense that it is subject to an extremely low rate of increase of lactic acid at a lower temperature. Thus finding has led to completion of the present invention.

According to the present invention, the *Lactobacillus bulgaricus* ATCC 11842 was incubated as parent strain on an isolated culture medium, the separate bacteria were inoculated on the culture medium of the cow's milk and incubated at 43° C. until the time the lactic acid content reached a level of 0.23 to 0.28%, after which the culture was cooled at once to isolate a variant *Lactobacillus bulgaricus* which is sensitive to a lower range of temperatures in the sense that it is subject to an increase in lactic acid content of 0.1% or less on preservation at 10° C. for 7 days.

The fermented milk and the lactic acid beverage that were manufactured by using the variant *Lactobacillus bulgaricus* exhibited superior properties during the cold preservation without deterioration in flavor due to the increase in the sour taste.

DESCRIPTION OF THE PREFERRED EMBODIMENT

According to one aspect of the present invention, there is provided a microorganism belonging to a variant *Lactobacillus bulgaricus* which is sensitive at lower temperature characterized in that it shows an increase in lactic acid contents of 0.1% or less when the biomass thereof is inoculated to a culture medium of the cow's milk, incubated at 43° C. until the amount of lactic acid reaches the level of 0.23 to 0.28%, the cooled and preserved at 10° C. for 7 days.

According to a further aspect of the present invention, there is provided a method for selecting a microorganism belonging to the variant *Lactobacillus bulgaricus* sensitive at a lower temperature comprising the steps of inoculating the strain *Lactobacillus bulgaricus* to a culture medium of the defatted milk, containing a yeast extract, incubating the culture twice on end, inoculating the activated strain to a culture medium of the cow's milk, incubating the resulting culture at 43° C. until the amount of lactic acid reaches the level of 0.23 to 0.28%, immediately cooling the resulting culture, preserving the cooled culture at 10° C. for 7 days, and selecting from the culture the strain showing an increase of lactic acid content of 0.1% or less under these conditions.

According to a further aspect of the present invention, there is provided a fermented milk or lactic acid beverage obtained by employing a microorganism belonging to a variant *Lactobacillus bulgaricus*. According to another aspect of the present invention, there is provided a method for producing the fermented milk or lactic acid beverage comprising the steps of inoculating the aforementioned microorganism as the starter to a starting material derived from the cow's milk and fermenting the resulting culture.

Figure 1:
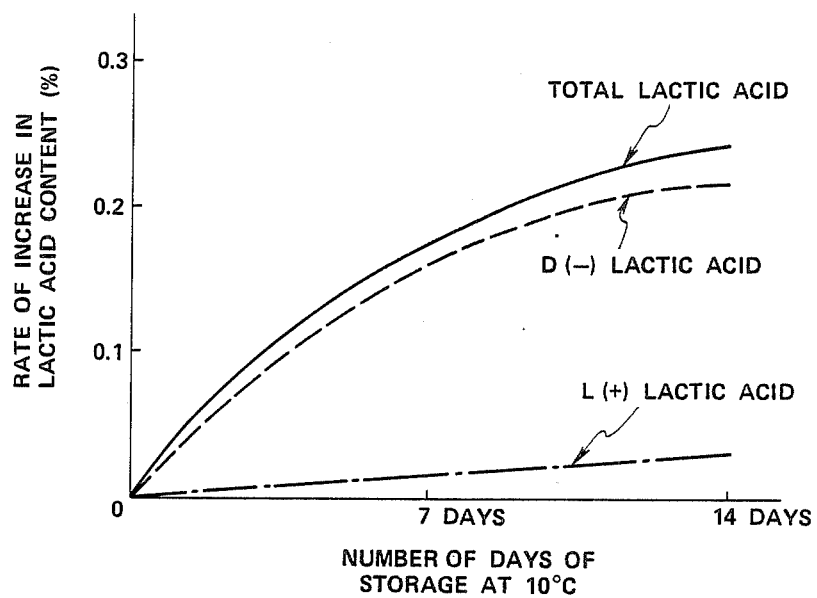
FIG. 1 is a chart showing the increase in lactic acid content in the yoghurt on preservation thereof at 10° C.

An increase in acidity of the yoghurt on cold preservation is mainly due to D(−) lactic acid produced by *Lactobacillus bulgaricus*. This can be found from an increase in the lactic acid content in a yoghurt when preserved at a lower temperature, said yoghurt having been produced by inoculating a yoghurt mix (starting material for yoghurt) with the strain *Lactobacillus bulgaricus* and the strain *Streptococcus thermophilus*, fermenting the resulting culture at 40° to 46° C. to produce lactic acid and preserving the resulting yoghurt at a lower temperature. FIG. 1 shows the increase of the D(−) lactic acid, L(+) lactic acid and the total lactic acid in the yoghurt preserved at 10° C. for about two weeks. It is noted that D(−) lactic acid is produced from *Lactobacillus bulgaricus* and L(+) lactic acid from *Streptococcus thermophilus*. It is seen from FIG. 1 that most of lactic acid produced on cold preservation is D(−) lactic acid. It is also seen that the increased sour taste in the yoghurt during cold preservation thereof is mainly ascribable to *Lactobacillus bulgaricus*.

The present inventors directed attention to this fact and conducted eager researches. As a result thereof, we succeeded in separating low-temperature-sensitive variant *Lactobacillus bulgaricus* showing an active lactic acid fermentation in the vicinity of 43° C. but producing only an extremely small amount of lactic acid during preservation at a lower temperature.

In our experiments, the strain *Lactobacillus bulgaricus* ATCC 11842 was incubated as the parent strain on the separate culture medium for separating the low-temperature-sensitive *Lactobacillus bulgaricus* of the present invention. More in detail, the strain *Lactobacillus bulgaricus* ATCC 11842 was inoculated on the MRS culture medium for incubation. A portion of the culture solution was added on the MRS culture medium containing the penicillin G potassium salt for incubation. A biomass separated from the culture solution was coated on the blood liver agar culture medium and the thus coated product was incubated under anaerobic conditions. The colonies appearing on the blood liver agar culture medium were incubated in a sterilized defatted milk containing the yeast extreact for two consecutive generations. This culture solution was inoculated on the culture medium of the cow's milk and the resulting culture was incubated at 43° C. until the lactic acid content reached the level of 0.23 to 0.28%. At this time the culture solution was cooled immediately and preserved at 10° C. for 7 days. The strain showing an increase of lactic acid of 0.1% or less on preservation at 10° C. for 7 days was selectively isolated.

It is noted that the MRS culture medium was prepared by mixing 10 g of peptone, 10 g of meat extract, 5 g of yeast extract, 20 g of grape sugar, 1.0 ml of Tween 80, 2.0 g of $K_2HPO_4$, 5 g of $CH_3COONa.3H_2O$, 2 g of ammonium citrate, 200 mg of $MgSO_4.7H_2O$ and 1000 ml of distilled water, adjusting the Ph value of the resulting mixture to 6.0 to 6.5 and sterilizing the mixture at 120° C. for 15 minutes. The culture medium of the cow's milk was prepared by providing a 95:2:3 mixture of cow's milk, skim milk powders and water for dissolving the skim milk powders and sterilizing the resulting solution by heating at 95° C. for 5 minutes.

This newly isolated microorganism had the following mycological properties and, while belonging to the *Lactobacillus bulgaricus*, was identified to be its variant from the following reason and denominated *Lactobacillus bulgaricus* OLL 1074.

Applicant has made a deposit of a culture of the aforesaid microorganism with an international depository authority, (Fermentation Research Institute Agency of Industrial Science and Technology, 1-3, Higashi 1 chome Yatabe-machi Tsukuba-gun Ibaraki-ken, 305 Japan) pursuant to the terms of the Budapest Treaty on the International Recognition of the Deposit of Mirororganisms for the Purposes of Patent Procedure, on June 25, 1985, under Deposit Number FERM BP-1041.

The new microorganism has the following mycological properties.

A. Morphological properties (1) It has a rod shape.
(2) It is not mobile.
(3) It has not spore.
(4) It shows the positive Gram's stain.
(5) It has metachromatic granules.

B. Growth state on the culture medium

As the microorganism was coated on the flat plate of the BL agar culture medium (Ei-ken) and incubated at 37° C. for 48 hours by the steel wool method, the cultrue showed an opaque R-type indefinite colony form.

C. Physiological properties (1) It shows negative properties in reducing nitrates.
(2) It shows negative properties in indol synthesis.
(3) It shows negative properties in gelatine liquefaction.
(4) It shows a negative catalase reaction.
(5) It shows negative properties in starch decomposition.
(6) It acts as facultative anaerobic bacteria with respect to oxygen.
(7) It produces D(−) lactic acid from glucose by homolactic acid fermentation without producing gases.
(8) It does not produce $CO_2$ from malates.
(9) It cannot be propagated at all or can only be weakly propagated at 25° C. on the MRS culture medium. However, it can be vigorously propagated at 45° C.

(10) It can or cannot decompose various carbohydrates. In the following, the marks (+) and (−) indicate positive and negative properties in this respect.
 (i) glucose—(+)
 (ii) lactose—(+)
 (iii) fructose—(+)
 (iv) mannose—(+)
 (v) galactose—(−)
 (vi) sucrose—(−)
 (vii) maltose—(−)
 (viii) cellobiose—(−)
 (ix) trehalose—(−)
 (x) melibiose—(−)
 (xi) raffinose—(−)
 (xii) melezitose—(−)
 (xiii) starch—(−)
 (xiv) mannitol—(−)
 (xv) sorbitol—(−)
 (xvi) esculin—(−)
 (xvii) salicin—(−)
 (xviii) amygdalin—(−)

By relying upon the Mitsuoka's method (Journal of Medical Technology 18, 1163 (1974)), the above properties were found to be identified with the mycological properties of the parent strain *Lactobacillus bulgaricus* ATCC 11842. However, the new microorganism was clearly different from the parent strain in the extremely low propagation properties thereof on the MRC culture medium at 25° C. and hence was recognized to be a variant showing a peculiar sensitivity at a lower temperature.

This *Lactobacillus bulgaricus* OLL 1074 showing peculiar sensitivity to a lower temperature was incubated for 10 consecutive generations and tested for its lactic acid producing properties at the lower temperature. The results are shown in the following Table 1. As seen from this Table, these properties of the various generations of the strain were necessarily low.

In the following Table, percent increase of lactic acid of the various generations of *Lactobacillus bulgaricus* OLL 1074 (FERM BP-1041) incubated on the skim milk culture medium is shown. Each of ten (10) tested generations was prepared by inoculating the culture of the preceding generation on the culture medium of the cow's milk at a rate of 2% of the culture solution based on the amount of the total culture medium and incubating the resulting culture at 43° C. to give a lactic acid content in the microorganism equal to ca. 0.25%, and the increase in the lactic acid content in the microorganism after preservation at 10° C. for 7 days was checked.

TABLE 1

| generation number | lactic acid content (%) in the cow's milk culture medium | | increase of lactic acid after preservation at 10 C. for 7 days |
|---|---|---|---|
| | before cold preservation | after preservation at 10 C. for 7 days | |
| 1 | 0.25 | 0.33 | 0.08 |
| 2 | 0.26 | 0.33 | 0.07 |
| 3 | 0.25 | 0.33 | 0.08 |
| 4 | 0.23 | 0.31 | 0.08 |
| 5 | 0.27 | 0.34 | 0.07 |
| 6 | 0.26 | 0.34 | 0.08 |
| 7 | 0.25 | 0.32 | 0.07 |
| 8 | 0.24 | 0.33 | 0.09 |
| 9 | 0.25 | 0.33 | 0.08 |
| 10 | 0.26 | 0.34 | 0.08 |

Figure 2:
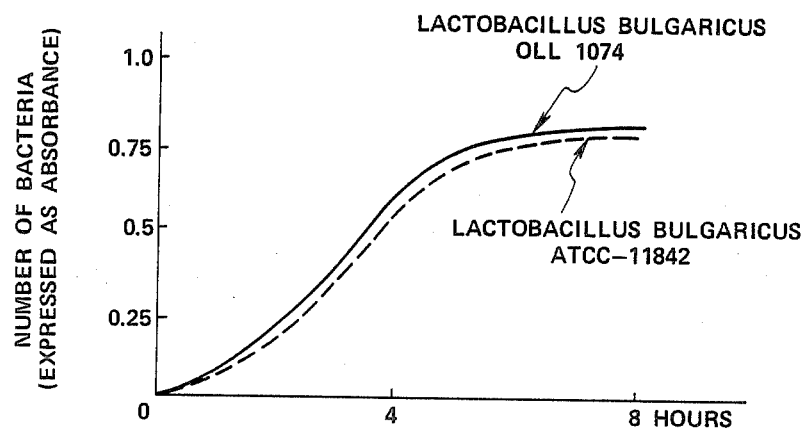
FIG. 2 is a chart showing a curve for the propagation of the bacteria on the MRS culture medium.
Figure 2:
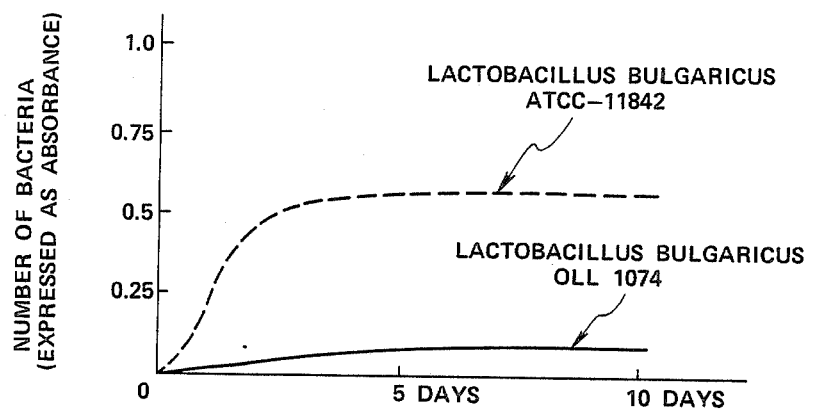

For further clarifying the difference between the present variant *Lactobacillus bulgaricus* showing sensitivity at a lower temperature (FERM BP-1041) and the parent strain *Lactobacillus bulgaricus* ATCC 11842, these two strains were inoculated on the MRS culture medium and incubated at 25° or 43° C. and the respective propagation curves were scrutinized. The results are shown in FIG. 2. As will be seen from this figure, there is no difference between the curves for 43° C., but a marked difference exists between those for 25° C.

Figure 3:
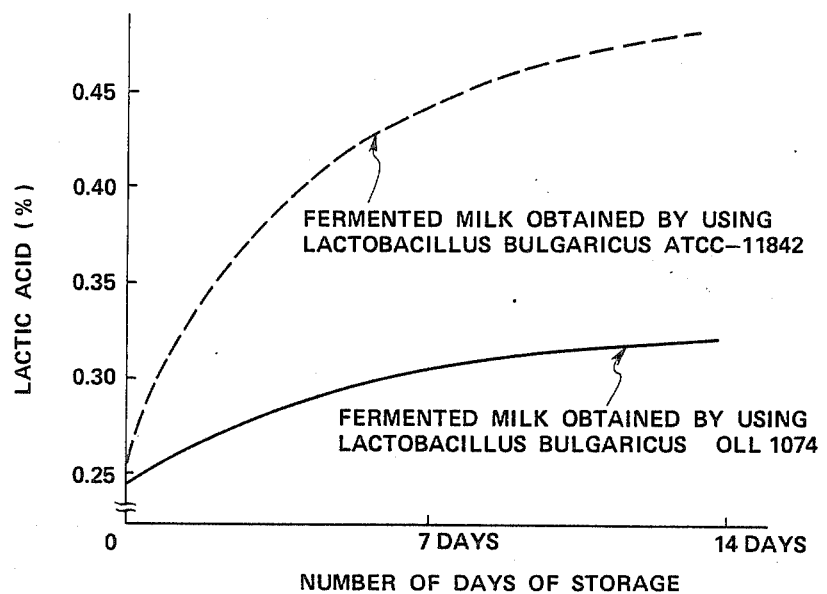
FIG. 3 is a chart showing a curve for changes in lactic acid content in the fermented milk preserved at 10° C.
Figure 4:
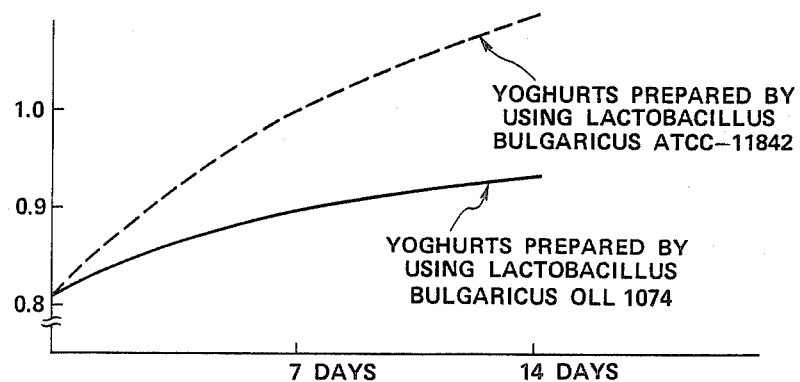
FIG. 4 is a chart showing a curve for changes in lactic acid content in the yoghurt prepared by using a mixed stater and preserved at 10° C.
Figure 4:
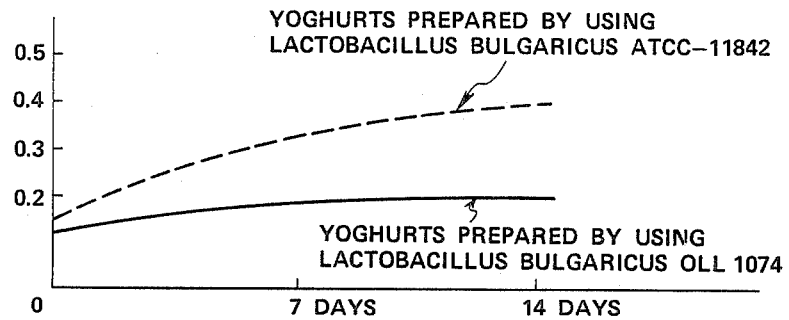

Then the defatted sterilized milk was inoculated with *Lactobacillus bulgaricus* OLL 1074 and the resulting culture was incubated at 43° C. The thus-obtained starter was inoculated in an amount of 2% based on the total cow's milk and the resulting culture was incubated at 43° C. for 4 hours to produce fermented milk. This fermented milk was preserved at 10° C. for 14 days and changes in lactic acid content thereof was scrutinized. The results are shown in FIG. 3. It is seen from this figure that only a minor amount of lactic acid is produced on cold preservation of the fermented milk obtained by using the strain *Lactobacillus bulgaricus* OLL 1074. The yoghurt was also produced with the use of a mixed starter of *Lactobacillus bulgaricus* OLL 1074 and *Streptococcus thermophilus* IAM-1047 and changes in the content of D(−) lactic acid (%) and in the acidity of the lactic acid (%) of the thus-produced yoghurt on preservation at 10° C. for 14 days were scrutinized. The results are shown in FIG. 4. It is seen from this figure that, when *Lactobacillus bulgaricus* OLL 1074 is used as the starter for yoghurt preparation, the sour taste proper to the fermented milk just after manufacture thereof is maintained during distribution and preservation periods since the rate of increase of the acidity and the yield of D(−) lactic acid during the cold preservation remain at lower values.

Other lactic acid bacteria employed in accordance with the present invention can include *Streptococcus thermophilus* IAM 1047, *Lactobacillus lactis*, Bifidobacterium, *Lactobacillus acidophilus* and *Lactobacillus casei*.

The present invention will be described with reference to several specific Examples thereof. It should be noted that these Examples are given only by way of illustration and are not intended for limiting the scope of the invention.

EXAMPLE 1

30 ml of an MRS culture medium was inoculated with *Lactobacillus bulgaricus* ATCC 11842 and incubation was carried out at 37° C. for 16 hours. 20 ml of this culture solution was added to 500 ml of an MRS culture medium containing 0.10 unit per ml of potassium salt of penicillin G and the culture was incubated at 25° C. for 48 hours. The culture solution was centrifuged at 5000 rpm for 15 minutes for collecting bacteria which were then suspended in sterilized physiological saline water. Each 0.1 ml fraction of the water was coated on a flat plate of blood liver agar (BL agar) and anaerobically incubated at 37° C. for 48 hours. The above described sequence of operations was repeated until the respective colonies were caused to exist on the BL agar flat plate. These colonies were inoculated in sterilized defatted milk containing 0.1 percent of the yeast extract and the resulting culture was incubated for two generations at 37° C. for 16 hours. The culture solution inoculated on a culture medium of the cow's milk at a rate of 2% based on the amount of the total culture medium and incubated at 43° C. until the time the lactic acid content reached a level of 0.23 to 0.28%. At this time, the culture medium was cooled immediately. From the thus incubated strains *Lactobacillus bulgaricus* OLL 1074 showing sensitivity at lower temperatures was isolated in such a manner that those strains showing an increase of lactic acid of less than 0.1% upon preservation at 10° C. for 7 days were selected.

EXAMPLE 2

The strain *Lactobacillus bulgaricus* OLL 1074 sensitive to low temperature and the strain *Streptococcus thermophilus* IAM-1047 were inoculated on the defatted sterilized milk and the resulting culture was incubated at 43° C. so as to be used as a starter for fermented milk. The starter was inoculated at a rate of 2% based on the total culture medium on a sterilized yoghurt mix, that is, a starting material for yoghurt, which is the sterilized cow's milk fortified with skim milk powders. The resulting culture was immediately incubated at 43° C. to an acidity of lactic acid of 0.8% and immediately cooled to produce the yoghurt. The fermentation time at 43° C. for this yoghurt was 3.5 hours similarly to the case of using the strain *Lactobacillus bulgaricus* ATCC 11842 as reference material. However, on preservation at a lower temperature of 25° C. or less, the product showed an increasse in the acidity less than half that of the reference strain. On preservation at 10° C. for 14 days, the rate of D(−) lactic acid in the total lactic acid amounted to 20.8% which was manifestly lower than the value of 50.4% for the reference material.

EXAMPLE 3

The strain *Lactobacillus bulgaricus* OLL 1074 sensitive to low temperature and the strain *Streptococcus thermophilus* IAM-1047 were inoculated to the defatted sterilized milk and the resulting culture was incubated at 43° C. so as to be used as a starter for the fermented milk. This starter was inoculated at a rate of 2% based on the total culture medium sterilized yoghurt mix, herein a sweetened sterilized cow's milk mixed with skim milk powders and saccharose. The resulting culture was immediately incubated at 43° C. until the time the acidity of lactic acid reached a level of 1.0%, at which time the culture was immediately cooled and mixed with 7.0% of chunks of sterilized fruit such as orange, strawberry or pineapple under agitation. The resulting mixture was charged into a container to a fruit yoghurt product. The fermentation period at 43° C. for this fruit yoghurt product was 4 hours which was same as that for the reference strain *Lactobacillus bulgaricus* ATCC 11842. However, the rate of increase of lactic acid contents upon preservation at 10° C. for 7 days was 0.08% for this product, thus indicating that the rate of increase of the sour taste on preservation at a lower temperature was significantly lowered.

EXAMPLE 4

The strain *Lactobacillus bulgaricus* OLL 1074 which is sensitive to a lower temperature was inoculated to a defatted sterilized milk and the resulting culture was incubated at 37° C. for 4 hours. Separately, a strain *Lactobacillus acidophilus* ATCC-4356 was inoculated to a defatted sterilized milk and the resulting culture medium was incubated at 35° C. for 20 hours. 60 kgs of a sterilized liquid mixture mainly composed of saccharose, CMC, perfume and organic acids (pH value: 3.5) and containing 14.0 kg of saccharose, 0.4 kg of CMC, 0.05 kg of perfume, 0.2 kg of citric acid, 0.05 kg of ascorbic acid and 46.0 kg of water, was prepared and blended with 40 kg of a liquid mixture consisting of equal amounts of the aforementioned two bacterial liquids. The resulting product was homogenized to a lactic acid beverage. Upon preservation at 10° C. for 7 days, the beverage showed no changes in acidity and had an excellent flavor with no changes in the numbers of two different lactic acid bacteria employed.

What is claimed is:

1. A microorganism belonging to a variant *Lactobacillus bulgaricus* which is sensitive at low temperatures, and which shows an increase in lactic acid contents of 0.1% or less when the biomass thereof is inoculated on a culture medium of cow's milk, the resulting culture is incubated at 43° C. until the lactic acid content reaches a level of 0.23% to 0.28%, then cooled, and preserved at 10° C. for 7 days.

2. A microorganism according to claim 1 being the strain *Lactobacillus bulgaricus* OLL 1074.

3. A method of selecting a microorganism belonging to the variant *Lactobacillus bulgaricus* sensitive at low temperatures, comprising the steps of: inoculating the strain *Lactobacillus bulgaricus* on a culture medium of defatted milk containing a yeast extract, incubating the resulting culture twice consecutively, inoculating the activated strain on a culture medium of cow's milk, incubating the resulting culture at 43° C. until the lactic acid reaches a level of 0.23 to 0.28%, immediately cooling and resulting culture, preserving the thus-cooled culture at 10° C. for 7 days, and selecting from the culture the strain showing an increase of lactic acid content of 0.1% or less.

* * * * *